United States Patent
Kobayashi

(10) Patent No.: US 8,344,357 B2
(45) Date of Patent: Jan. 1, 2013

(54) 3-TERMINAL ELECTRONIC DEVICE AND 2-TERMINAL ELECTRONIC DEVICE INCLUDING AN ACTIVE LAYER INCLUDING NANOSHEETS

(75) Inventor: Toshiyuki Kobayashi, Kanagawa (JP)

(73) Assignee: Sony Corporation, Tokyo (JP)

( * ) Notice: Subject to any disclaimer, the term of this patent is extended or adjusted under 35 U.S.C. 154(b) by 84 days.

(21) Appl. No.: 12/868,902

(22) Filed: Aug. 26, 2010

(65) Prior Publication Data

US 2011/0057168 A1 Mar. 10, 2011

(30) Foreign Application Priority Data

Sep. 10, 2009 (JP) ................. P2009-209842

(51) Int. Cl.
*H01L 29/06* (2006.01)
(52) U.S. Cl. ........ 257/24; 257/9; 257/E29.168; 257/E29.245; 977/936; 977/953; 977/755
(58) Field of Classification Search .............. 257/24, 257/9, E29.168, E29.245; 977/936, 953, 977/755
See application file for complete search history.

(56) References Cited

U.S. PATENT DOCUMENTS

2010/0028681 A1* 2/2010 Dai et al. .................. 428/408

OTHER PUBLICATIONS

Cristina Go'Mes-Navarro et al., Nano Letters 7, 3499 (2007).
G. Eda et al., Nature Nanotechnology 3, 270 (2008).
S. Wang et al., Advanced Materials 20, 3440 (2008).
G. Lu et al., Applied Physics Letters 94, 08311 (2009).
P. Joensen et al., Mat. Res. Bull., vol. 21, pp. 457-461, 1986.
J. Kedzierski et al., IEEE Transactions on Electron Devices, vol. 55, No. 8, Aug. 2008.

* cited by examiner

*Primary Examiner* — Marc Armand
*Assistant Examiner* — Eva Yan Montalvo
(74) *Attorney, Agent, or Firm* — K&L Gates LLP

(57) ABSTRACT

A 3-terminal electronic device includes: a control electrode; a first electrode and a second electrode; and an active layer that is provided between the first electrode and the second electrode and is provided to be opposed to the control electrode via an insulating layer. The active layer includes a collection of nanosheets. When it is assumed that the nanosheets have an average size $L_S$ and the first electrode and the second electrode have an interval D therebetween, $L_S/D \geq 10$ is satisfied.

6 Claims, 7 Drawing Sheets

FIG.1A [Step-120]
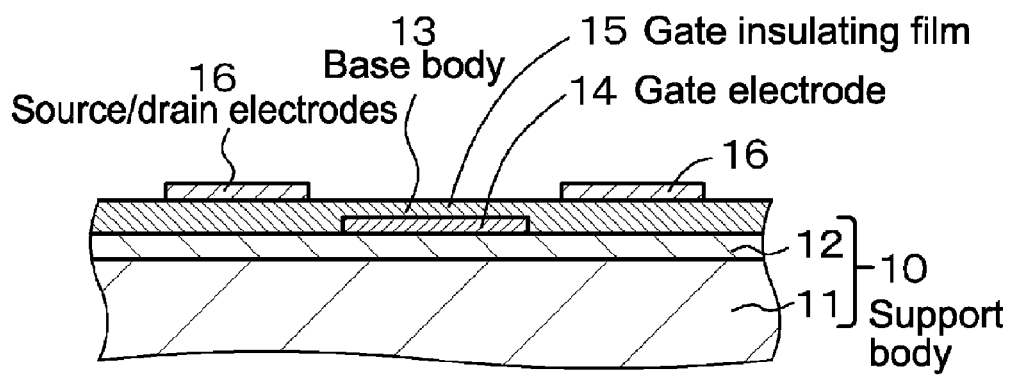
FIG.1B [Step-130]
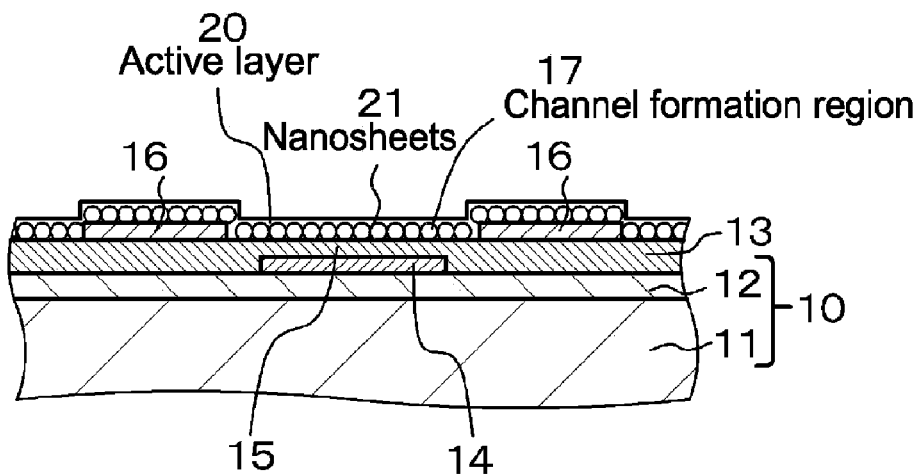

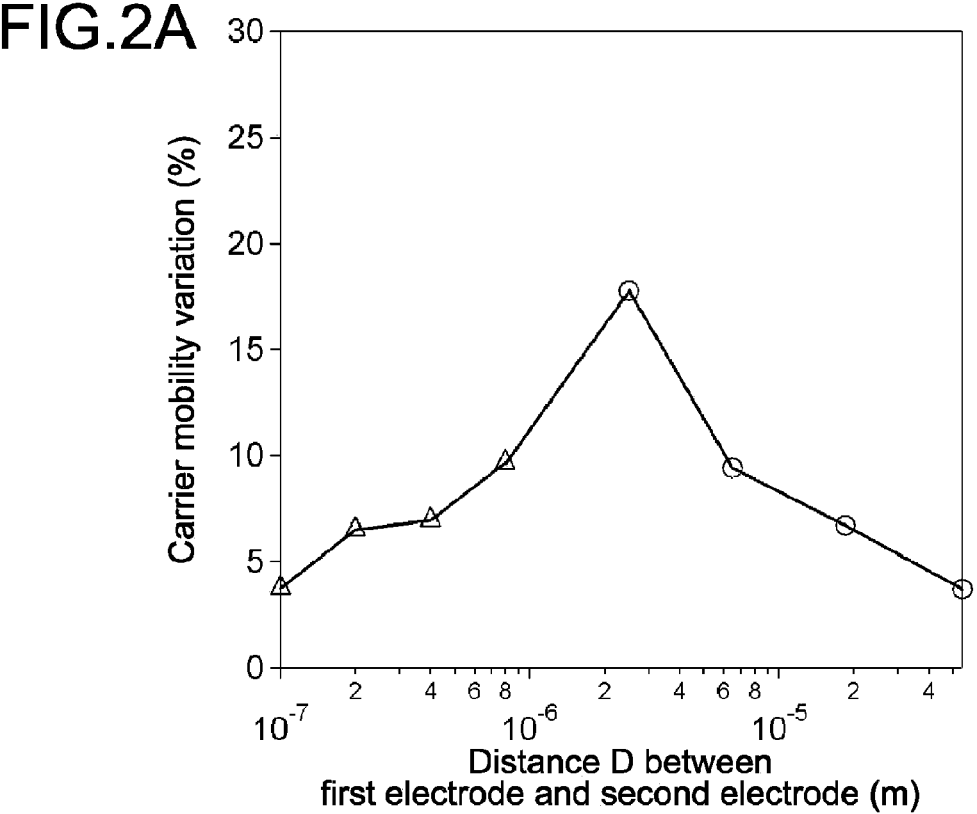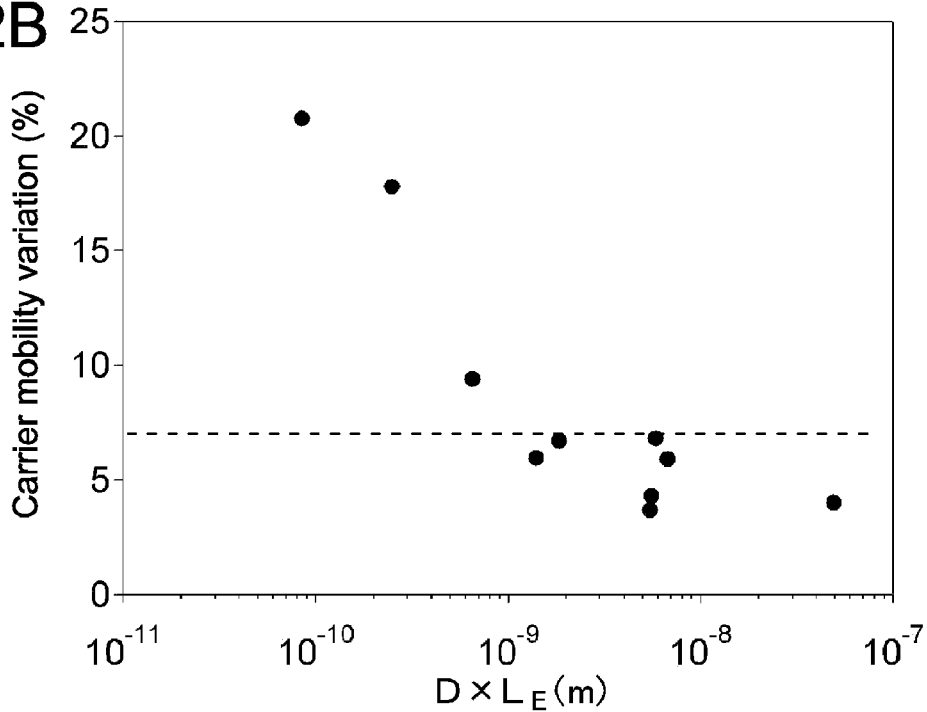

FIG.4A [Step-210]
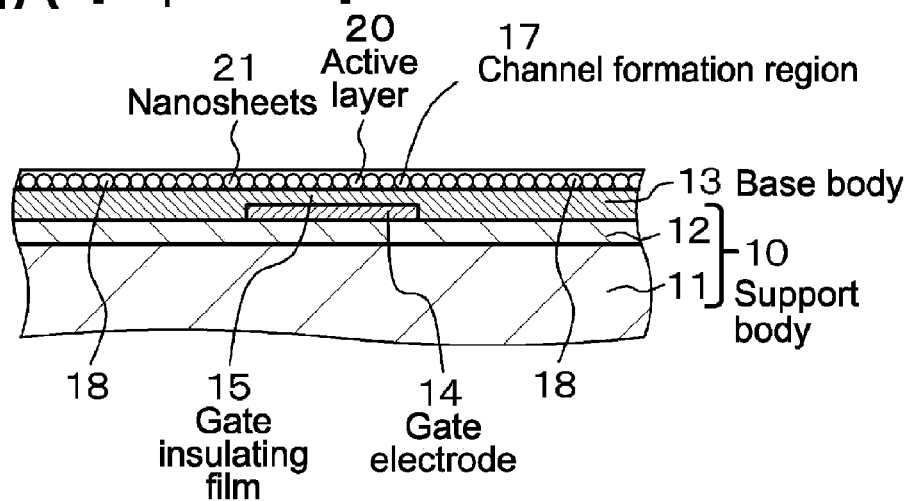
FIG.4B [Step-220]
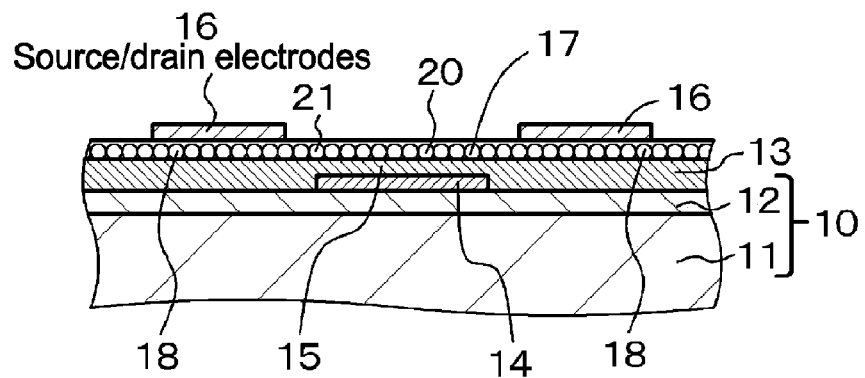

FIG.5A [Step-300]
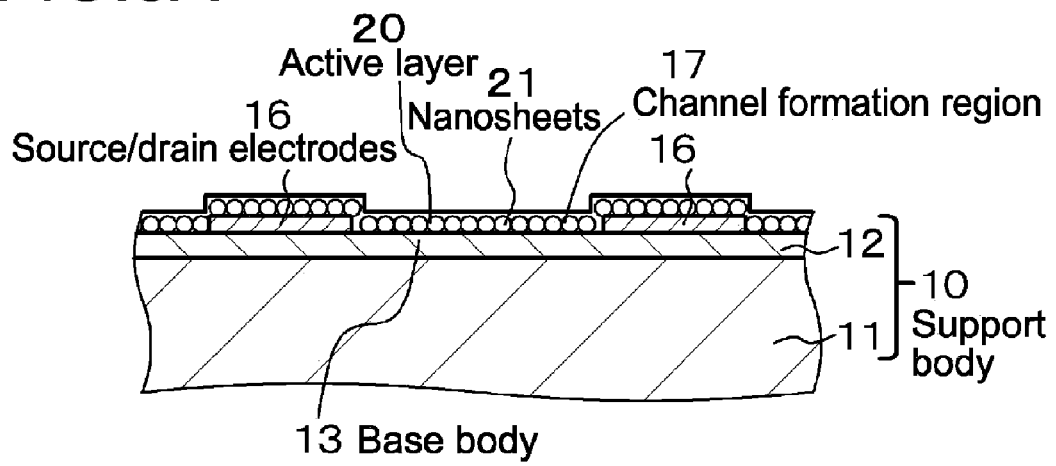
FIG.5B [Step-320]
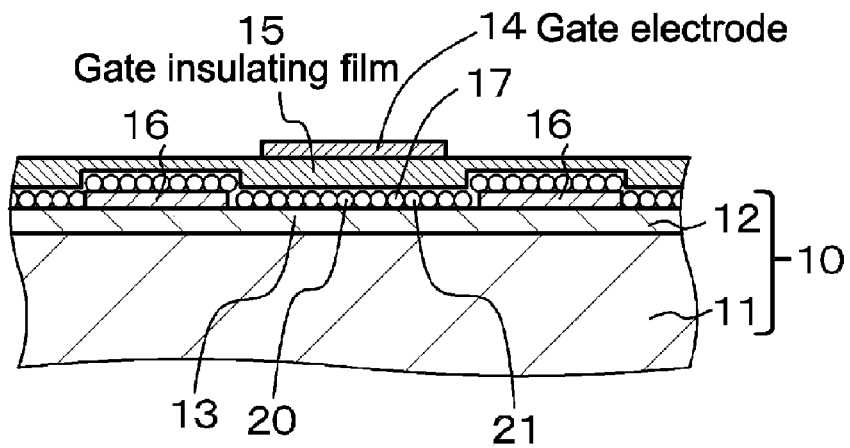

FIG.6A [Step-400]
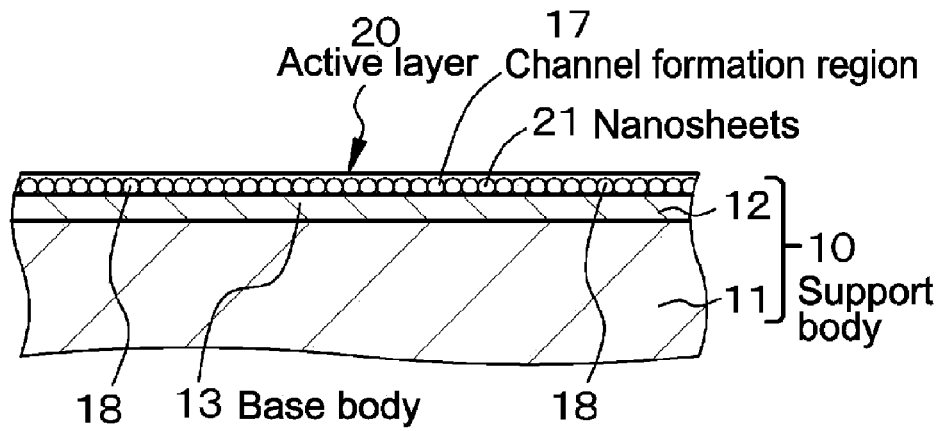
FIG.6B [Step-410]
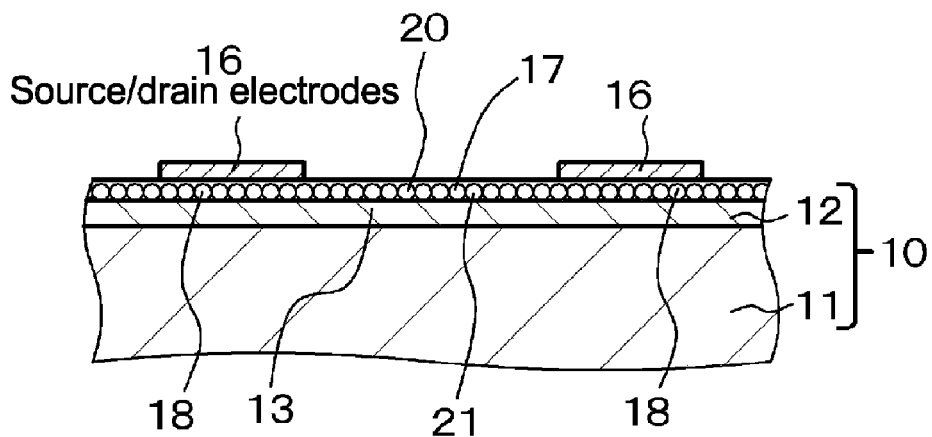
FIG.6C [Step-420]
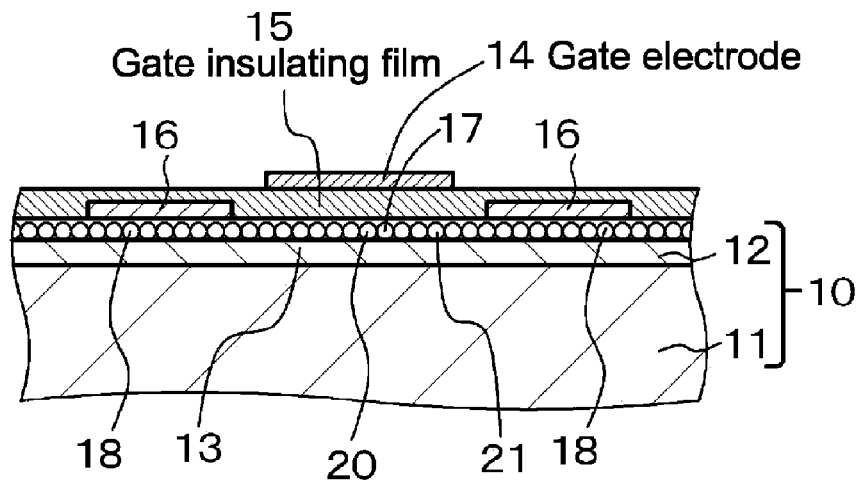

3-TERMINAL ELECTRONIC DEVICE AND 2-TERMINAL ELECTRONIC DEVICE INCLUDING AN ACTIVE LAYER INCLUDING NANOSHEETS

CROSS REFERENCES TO RELATED APPLICATIONS

The present application claims priority to Japanese Priority Patent Application JP 2009-209842 filed in the Japan Patent Office on Sep. 10, 2009, the entire content of which is hereby incorporated by reference.

BACKGROUND

The present application relates to a 3-terminal electronic device constituting a thin-film transistor or the like and a 2-terminal electronic device constituting a chemical substance sensor or the like.

In a thin-film transistor (TFT), a technique has been considered by which nanosheets made of graphene or reduced graphene oxide (RGO) are fully arranged on a substrate to thereby form a channel formation region (see Nano Letters 7, 3499 (2007), Nature Nanotechnology 3, 270 (2008), and Advanced Materials 20, 3440 (2008), for example). Furthermore, a gas sensor using nanosheets made of graphene or RGO is known, for example, from Applied Physics Letters 94, 083111 (2009). RGO is a nanosheet obtained by chemically reducing an oxidized graphene sheet obtained by oxidizing graphite. Since RGO includes various functional groups forming $sp^3$ bond, RGO is advantageous in that RGO is soluble in various solvents at high concentration, although RGO has a lower conductivity than graphene.

SUMMARY

By the way, in nanosheets, electrical resistance between nanosheets is higher than that in the nanosheets. Thus, when a TFT channel formation region is constituted of nanosheets and when a TFT channel length is approximately equal to the average size of the nanosheets, the channel formation region has significantly-varied electrical resistance value among nanosheets, which causes a variation of characteristics (e.g., carrier mobility). Furthermore, a sensor also has a significantly-varied electrical resistance value among nanosheets provided between two electrodes, which causes a variation of the sensor characteristics.

In view of the foregoing, it is desirable to provide a 3-terminal electronic device and a 2-terminal electronic device that have a small characteristic variation.

According to a first embodiment, there is provided a 3-terminal electronic device including: (A) a control electrode; (B) a first electrode and a second electrode; and (C) an active layer that is provided between the first electrode and the second electrode and is provided to be opposed to the control electrode via an insulating layer.

The active layer includes a collection of nanosheets.

When it is assumed that the nanosheets have an average size $L_S$ and the first electrode and the second electrode have an interval D therebetween, $L_S/D \geq 10$ is satisfied.

According to a second embodiment, there is provided a 3-terminal electronic device including: (A) a control electrode; (B) a first electrode and a second electrode; and (C) an active layer that is provided between the first electrode and the second electrode and is provided to be opposed to the control electrode via an insulating layer.

The active layer includes a collection of nanosheets.

When it is assumed that the nanosheets have an average size $L_S$, the first electrode and the second electrode have an interval D therebetween, and the first electrode and the second electrode each have a length $L_E$, $D \times L_E \geq 3 \times 10^2 \times L_S^2$ is satisfied.

According to a third embodiment, there is provided a 2-terminal electronic device including: (A) a first electrode and a second electrode; and (B) an active layer that is provided between the first electrode and the second electrode.

The active layer includes a collection of nanosheets.

When it is assumed that the nanosheets have an average size $L_S$ and the first electrode and the second electrode have an interval D therebetween, $L_S/D \geq 10$ is satisfied.

According to a fourth embodiment, there is provided a 2-terminal electronic device including: (A) a first electrode and a second electrode; and (B) an active layer that is provided between the first electrode and the second electrode.

The active layer includes a collection of nanosheets.

When it is assumed that the nanosheets have an average size $L_S$, the first electrode and the second electrode have an interval D therebetween, and the first electrode and the second electrode each have a length $L_E$, $D \times L_E \geq 3 \times 10^2 \times L_S^2$ is satisfied.

In the 3-terminal electronic device according to the first embodiment or the 2-terminal electronic device according to the third embodiment, $L_S/D \geq 10$ is satisfied. Specifically, the first electrode and the second electrode have therebetween a nanosheet sufficiently-larger than an interval between the first electrode and the second electrode. In the 3-terminal electronic device according to the second embodiment or the 2-terminal electronic device according to the fourth embodiment, $D \times L_E \geq 3 \times 10^2 \times L_S^2$ is satisfied. Specifically, a product of the interval D between the first electrode and the second electrode and the length $L_E$ of the first electrode and the second electrode (i.e., an area occupied by the active layer) is $3 \times 10^2$ times or more larger than the average area of the nanosheets. In other words, the active layer includes a great number of (or $3 \times 10^2$ or more) nanosheets. This can consequently suppress the variation of the electrical resistance value of the active layer provided between the first electrode and the second electrode, and suppress the characteristic variation of the 3-terminal electronic device (e.g., variation of carrier mobility) and the characteristic variation of the 2-terminal electronic device.

These and other objects, features and advantages of the present application will become more apparent in light of the following detailed description of best mode embodiments thereof, as illustrated in the accompanying drawings.

Additional features and advantages are described herein, and will be apparent from the following Detailed Description and the figures.

BRIEF DESCRIPTION OF THE FIGURES

FIGS. 1A and 1B are schematic partial end views illustrating a base body for example, for explaining the outline of a manufacture method for a 3-terminal electronic device of Example 1;

FIGS. 2A and 2B are graphs showing evaluation results of the relation between $L_S/D$ and a carrier mobility variation and the relation between $D \times L_E$ and a carrier mobility variation, respectively;

FIGS. 4A and 4B are schematic partial end views illustrating a base body for example, for explaining the outline of a manufacture method for a 3-terminal electronic device of Example 2;

FIGS. 5A and 5B are schematic partial end views illustrating a base body for example, for explaining the outline of a manufacture method for a 3-terminal electronic device of Example 3;

FIGS. 6A to 6C are schematic partial end views illustrating a base body for example, for explaining the outline of a manufacture method for a 3-terminal electronic device of Example 4.

DETAILED DESCRIPTION

The present application is described below in detail with reference to the drawings according to an embodiment. The detailed description is provided as follows:

1. General description of 3-terminal electronic device and 2-terminal electronic device according to first embodiment and second embodiment of present application
2. Example 1 (3-terminal electronic device according to first embodiment and second embodiment of present application)
3. Example 2 (Modification of Example 1)
4. Example 3 (Modification of Example 1)
5. Example 4 (Modification of Example 1)
6. Example 5 (2-terminal electronic device according to first embodiment and second embodiment of present application and others)

[General description of 3-terminal electronic device and 2-terminal electronic device according to first embodiment and second embodiment of present application]

Figure 3:
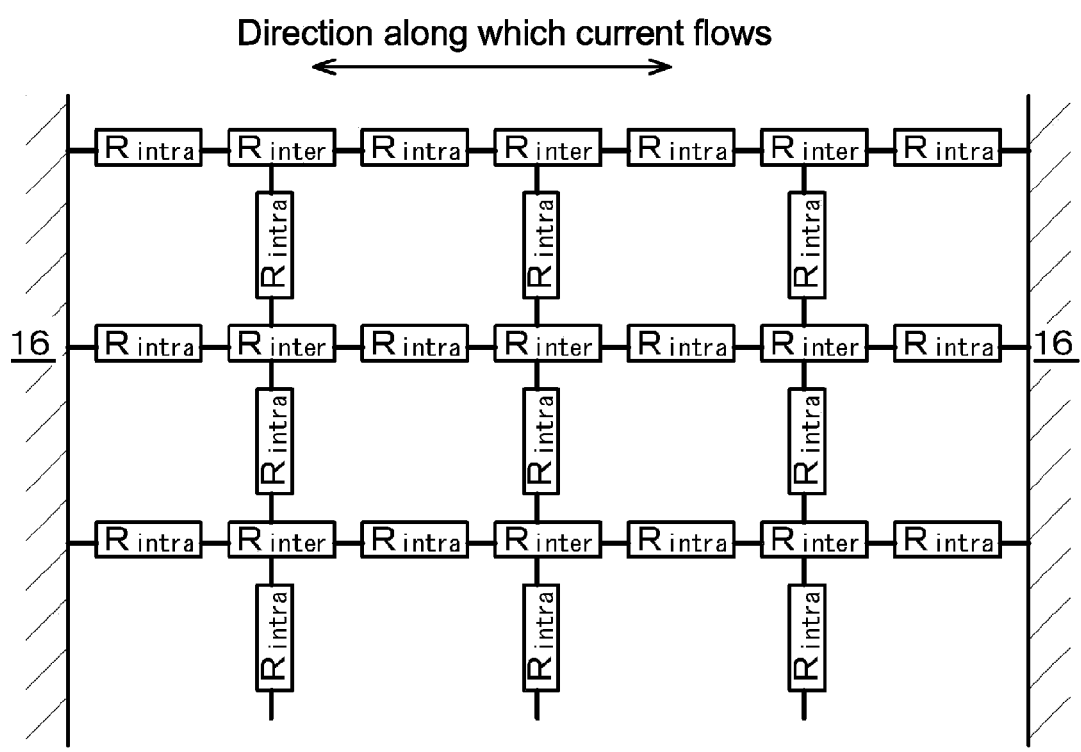
FIG. 3 is a schematic diagram illustrating the configuration of a sheet resistance value $R_{sheet}$ of a nanosheet collection (a thin film constituted of a great number of nanosheets)

In a 3-terminal electronic device or a 2-terminal electronic device according to a first embodiment or a second embodiment (hereinafter, collectively referred to simply as "electronic device of the present application" in some cases), a nanosheet means material for which one side has a length from tens of nanometers to hundreds of micrometers and the thickness is a few atomic layers or less. Examples of typical nanosheets include a nanosheet made of graphene of one layer of carbon atoms (including reduced graphene oxide, RGO) and a nanosheet made of semiconductor material such as $MoS_2$, $SnS_2$, and $GaSe$. By dispersing these nanosheets in a solvent, a large-area thin film can be formed based on a solution process (e.g., coating method). When nanosheets are used to form a thin film on a base body by a solution process, the nanosheets are deposited (or layered) on the base body to cover the base body. Thus, electrons can conduct from a nanosheet to another nanosheet to thereby traverse electrodes. At this time, a nanosheet collection (a thin film constituted of a great number of nanosheets) has a sheet resistance value $R_{sheet}$ of the sum of $(R_{intra}+R_{inter})$ (see the schematic view of FIG. 3). In the formula, $R_{intra}$ represents an electrical resistance value in the nanosheets and $R_{inter}$ represents an electrical resistance value between nanosheets. The reason why the sheet resistance value $R_{sheet}$ is the sum of $R_{intra}+R_{inter}$ is, as shown in FIG. 3, that many serial connections of $(R_{intra}+R_{inter})$ exist in parallel. In FIG. 3, resistance components $(R_{intra})$ vertically provided to a direction along which current flows have no current flowing therein (or a very small amount of current flows therein) and thus can be ignored.

An average nanosheet size $L_S$ can be obtained by calculating a nanosheet area S by the observation of nanosheets with a microscope having an appropriate magnification to calculate the average value of the square root of the area S.

The 3-terminal electronic device according to the first embodiment or the second embodiment may be a field effect transistor (more specifically, thin-film transistor). A 2-terminal electronic device according to the first embodiment or the second embodiment may be, for example, a chemical substance sensor for sensing $NO_2$ gas, $O_2$ gas, $NH_3$ gas, styrene gas, hexane gas, octane gas, decane gas, and trimethylbenzene gas. When nanosheets are used for TFT or a chemical substance sensor, there may be a case where the function of nanosheets does not appear if an active layer does not have a thickness reduced to about one atomic layer. For example, since graphene has a high carrier concentration, there may be a case where current modulation by a field effect is not obtained without an active layer having a thickness of a few atomic layers or less. Furthermore, since a chemical substance sensor needs to have an increased specific surface area, the active layer (chemical substance sensing layer) desirably has a thickness of one layer.

The field effect transistor can be a bottom gate/bottom contact-type, a bottom gate/top contact-type, a top gate/bottom contact-type, and a top gate/top contact-type, for example. By using a solution in which nanosheets are dispersed to form an active layer on a base body based on the coating method, a channel formation region in the field effect transistor can be obtained from a collection of nanosheets.

More specifically, the bottom gate/bottom contact-type field effect transistor includes:
(a) a gate electrode formed on a support body (which corresponds to a control electrode);
(b) a gate insulating film formed on the gate electrode and the support body (which corresponds to an insulating layer and also corresponds to a base body);
(c) source/drain electrodes formed on the gate insulating film (which correspond to a first electrode and a second electrode); and
(d) a channel formation region that is provided between the source/drain electrodes, formed on the gate insulating film, and composed by an active layer.

The bottom gate/top contact-type field effect transistor includes:
(a) a gate electrode formed on a support body (which corresponds to a control electrode);
(b) a gate insulating film formed on the gate electrode and the support body (which corresponds to an insulating layer and also corresponds to a base body);
(c) a channel formation region constituting layer that is formed on the gate insulating film and includes a channel formation region composed by an active layer; and
(d) source/drain electrodes formed on the channel formation region constituting layer (which correspond to the first electrode and the second electrode).

The top gate/bottom contact-type field effect transistor includes:
(a) source/drain electrodes formed on a base body (which correspond to the first electrode and the second electrode);
(b) a channel formation region that is formed on a base body between the source/drain electrodes and is composed by an active layer;
(c) a gate insulating film that is formed on the source/drain electrodes and the channel formation region (which corresponds to an insulating layer); and
(d) a gate electrode formed on the gate insulating film (which corresponds to a control electrode).

The top gate/top contact-type field effect transistor includes:

(a) a channel formation region constituting layer that is formed on a base body and includes a channel formation region composed by an active layer;

(b) source/drain electrodes formed on the channel formation region constituting layer (which correspond to the first electrode and the second electrode);

(c) a gate insulating film formed on the source/drain electrodes and the channel formation region (which corresponds to an insulating layer); and (d) a gate electrode formed on the gate insulating film (which corresponds to a control electrode).

In the electronic device according to the embodiments of the present application, examples of the coating method for forming an active layer include: a spin coating method; a dipping method; a cast method; various printing methods such as a screen printing method, an ink jet printing method, an offset printing method, and a gravure printing method; a stamp method; a spray method; and various coating methods such as an air doctor coater method, a blade coater method, a rod coater method, a knife coater method, a squeeze coater method, a reverse roll coater method, a transfer roll coater method, a gravure coater method, a kiss coater method, a cast coater method, a spray coater method, a slit orifice coater method, and a calendar coater method. Examples of the solvent for dispersing nanosheets include nonpolar or low-polarity organic solvents such as water, toluene, chloroform, hexane, methanol, and ethanol, or polar solvents such as DMF (N,N-dimethylformamide) and NMP (N-methylpyrrolidone).

The base body can be formed of silicon oxide-base material (e.g., $SiO_x$ or spin on glass (SOG)); silicon nitride ($SiN_Y$); silicon oxynitride (SiON); aluminum oxide ($Al_2O_3$); or a metal oxide high-dielectric insulating film. When the base body is formed of these materials, the base body only needs to be formed on a support body (or above the support body) appropriately selected from among the following materials. Specifically, examples of the support body or a base body other than the above-described base body include organic polymer (having the form of high-polymer material such as a flexible plastic film, plastic sheet, and plastic substrate that are formed of high-polymer material), including polymethylmethacrylate (polymethylmethacrylate, PMMA), polyvinyl alcohol (PVA), polyvinyl phenol (PVP), polyether sulfone (PES), polyimide, polycarbonate (PC), polyethylene terephthalate (PET), and polyethylene naphthalate (PEN). By using the base body formed of flexible high-polymer material as described above, the electronic device according to the embodiments of the present application can be mounted in or integrated with a display apparatus or an electronic apparatus having a curved shape, for example. Alternatively, examples of the base body (or support body) also include various glass substrates or quartz substrates, various glass substrates on which an insulating film is formed, a quartz substrate on which an insulating film is formed, a silicon substrate on which an insulating film is formed, a conductive substrate (a substrate made of metal such as gold, aluminum, and stainless steel, or alloy, a substrate made of high orientation graphite) on which an insulating film is formed.

In the electronic device according to the embodiments of the present application, the control electrode, the first electrode, the second electrode, and various optionally-formed wirings may be made of materials such as metal (e.g., platinum (Pt), gold (Au), palladium (Pd), chromium (Cr), nickel (Ni), aluminum (Al), silver (Ag), tantalum (Ta), tungsten (W), copper (Cu), titanium (Ti), indium (In), tin (Sn), iron (Fe), cobalt (Co), and molybdenum (Mo)), alloy including these metal elements, conductive particles made of these metals, conductive particles of alloy including these metals, and conductive substance such as polysilicon including impurities, or may also have a layered structure of layers including these elements. Furthermore, the control electrode, the first electrode, the second electrode, and various wirings may also be made of organic material (conductive high polymer) such as poly(3,4-ethylenedioxythiophene)/polystyrene sulfonic acid [PEDOT/PSS].

In the electronic device according to the embodiments of the present application, the control electrode, the first electrode, the second electrode, and various wirings may be formed, depending on the constituting materials thereof, by any of: physical vapor deposition (PVD); various chemical vapor deposition (CVD) including MOCVD method; the spin coating method; the dipping method; the cast method; various printing methods described above; the stamp method; various coating methods described above; a lift off method; a sol-gel method; an electrodeposition method; a shadow mask method; a plating method such as an electrolytic plating method, an electroless plating method, or a combination of them; and a spray method as well as a combination of an optional patterning technique. The PVD method may be, for example, (a) various vacuum vapor deposition methods such as an electronic beam heating method, a resistance heating method, and a flash evaporation, (b) a plasma vapor deposition method, (c) various sputtering methods such as a dipole sputtering method, a DC (direct current) sputtering method, a DC magnetron sputtering method, a high-frequency sputtering method, a magnetron sputtering method, an ion beam sputtering method, and a bias sputtering method, and (d) various ion plating methods such as a DC method, an RF method, a multi-cathode method, an activation reaction method, an electric field deposition method, a high-frequency ion plating method, and a reactive ion plating method.

Furthermore, in the electronic device according to the embodiments of the present application, the insulating layer (which may correspond to the base body) and the gate insulating film may be formed of materials including not only an inorganic insulating material exemplified by a metal oxide high-dielectric insulating film such as silicon oxide-base material; silicon nitride (SiNy); and oxidized aluminum (Al2O3), but also an organic insulating material (organic polymer) exemplified by linear hydrocarbons in which one end has a functional group that can be bonded to the control electrode (e.g., polymethylmethacrylate (PMMA); polyvinyl phenol (PVP); polyvinyl alcohol (PVA); polyimide; polycarbonate (PC); polyethylene terephthalate (PET); polystyrene; silanol derivative (silane coupling agent) such as N-2 (aminoethyl) 3-aminopropyltrimethoxysilane (AEAPTMS), 3-mercapto propyl trimethoxy silane (MPTMS), or octadecyltrichlorosilane (OTS); octadecanethiol; or dodecyl isocyanate) or a combination thereof. Silicon oxide-base material may be, for example, oxidized silicon (SiOX), BPSG, PSG, BSG, AsSG, PbSG, silicon oxynitride (SiON), SOG (spin on glass), or a low-permittivity SiO2-base material (e.g., polyarylether, cycloperfluorocarbon polymer and benzocyclobutene, cyclic fluorine resin, polytetrafluoroethylene, arylether fluoride, polyimide fluoride, amorphous carbon, and organic SOG).

The insulating layer and the gate insulating film may be formed by any of: various PVD methods described above; various CVD methods; a spin coating method; various printing methods described above; various coating methods described above; the dipping method; a casting method; the sol-gel method; the electrodeposition method; the shadow mask method; and the spray method. Alternatively, the insulating layer and the gate insulating film may also be formed by oxidizing or nitriding the surface of the control electrode or may also be obtained by forming an oxidized film or a nitride film on the surface of the control electrode. The surface of the control electrode may be oxidized, depending on the material constituting the control electrode, by an oxidation method using O2 plasma or an anode oxidation method, for example. The surface of the control electrode may be nitrided, depending on the material constituting the control electrode, by a nitriding method using N2 plasma, for example. Alternatively, with regard to an Au electrode, for example, by insulating molecules having a functional group that may chemically form a bond with the control electrode, such as strait-chain hydrocarbons in which one end is modified by a mercapto group, a method such as the dipping method also can be used to cover the surface of the control electrode in the self-organizing manner to thereby form an insulating layer or a gate insulating film on the surface of the control electrode. Alternatively, the surface of the control electrode can also be modified by a silanol derivative (silane coupling agent) to thereby form an insulating layer or a gate insulating film.

When the electronic device is applied to or used for a display apparatus and various electronic apparatuses, the electronic device may be a monolithic integrated circuit in which the support body is integrated with a great number of electronic devices. Alternatively, the respective electronic devices may also be cut and individuated and may also be used as discrete parts. The electronic device may also be sealed by resin.

Example 1

Example 1 relates to a 3-terminal electronic device according to the first embodiment and the second embodiment (specifically, a field effect transistor and more specifically, a thin-film transistor (TFT)). A 3-terminal electronic device according to Example 1 or Example 2 to Example 4 to be described later is a 3-terminal electronic device including:

(A) a control electrode (which corresponds to a gate electrode 14);

(B) a first electrode and a second electrode (which correspond to source/drain electrodes 16); and (C) an active layer 20 that is provided between the first electrode and the second electrode and is provide to be opposed to the control electrode 14 via an insulating layer (which corresponds to a gate insulating film 15).

More specifically, the 3-terminal electronic device of Example 1 is a bottom gate/bottom contact-type thin-film transistor (TFT) as shown in the schematic partial cross-sectional view of FIG. 1B, including:

(a) the gate electrode 14 formed on a support body 10 (which corresponds to a control electrode);

(b) the gate insulating film 15 formed on the gate electrode 14 and the support body 10 (which corresponds to an insulating layer and a base body 13);

(c) the source/drain electrodes 16 formed on the gate insulating film 15 (which correspond to the first electrode and the second electrode); and (d) a channel formation region 17 that is provided between the source/drain electrodes 16, formed on the gate insulating film 15, and formed of the active layer 20.

The active layer 20 (the channel formation region 17) is formed of a collection of nanosheets 21 (specifically, a collection of nanosheets 21 made of reduced graphene oxide (RGO)). Here, the nanosheets having an average size $L_S$ of 2 μm was used. In the drawings, the nanosheets 21 may be shown by circles for convenience.

According to the configuration requirements of the 3-terminal electronic device according to the first embodiment, the 3-terminal electronic device of Example 1 satisfies $L_S/D \geqq 10$ when assuming that the nanosheet average size is $L_S$ and an interval between the first electrode and the second electrode is D. Specifically, a 3-terminal electronic device (thin-film transistor) was prepared for which the interval D between the first electrode and the second electrode (an interval between the source/drain electrodes 16) was 0.2 μm. A length $L_C$ of the control electrode (the gate electrode 14) and a length $L_E$ of the first electrode and the second electrode were set to 100 μm. Then, in order to investigate the relation between $L_S/D$ and the carrier mobility, various TFTs were prototyped. Specifically, under the fixed condition of $L_C$=100 μm, various TFTs having different Ds were prototyped and the carrier mobility variation was evaluated, the results of which are shown in FIG. 2A. The carrier mobility variation means a value obtained by dividing the standard deviation (σ) of the carrier mobility measurement value by an average value of the carrier mobility measurement value.

As can be seen from FIG. 2A, an increase in the value of $L_S/D$ causes a decrease in the carrier mobility variation. Specifically, by providing nanosheet between the source/drain electrodes 16 that is sufficiently larger than the interval between the source/drain electrodes 16, the active layer 20 provided between the source/drain electrodes 16 can be suppressed from having a variation of the electrical resistance value, thus suppressing a variation of the carrier mobility of the 3-terminal electronic device. As described above, when the source/drain electrodes 16 includes therebetween nanosheets sufficiently larger than the interval between the source/drain electrodes 16, the sheet resistance value $R_{sheet}$ of the active layer 20 between the source/drain electrodes 16 is mostly $R_{intra}$. Thus, a variation of the electrical resistance value of the active layer 20 can be suppressed.

Furthermore, according to the configuration requirements of the 3-terminal electronic device according to the second embodiment, the 3-terminal electronic device of Example 1 satisfies $D \times L_E \geqq 3 \times 10^2 \times L_s^2$. Specifically, 3-terminal electronic devices shown in Table 1 below were prototyped and the carrier mobility variation was evaluated, the results of which are shown in FIG. 2B.

TABLE 1

| Sample | D (μm) | $L_E$ (μm) | $D \times L_E$ (m$^2$) | $D \times L_E/L_s^2$ |
|---|---|---|---|---|
| 1 | 2.5 | 34 | $8.5 \times 10^{-11}$ | $2.1 \times 10$ |
| 2 | 2.5 | 100 | $2.5 \times 10^{-10}$ | $6.3 \times 10$ |
| 3 | 2.5 | 560 | $1.4 \times 10^{-9}$ | $3.5 \times 10^2$ |
| 4 | 2.5 | 2700 | $6.8 \times 10^{-9}$ | $1.7 \times 10^3$ |
| 5 | 6.5 | 100 | $6.5 \times 10^{-10}$ | $1.6 \times 10^2$ |
| 6 | 6.5 | 900 | $5.9 \times 10^{-9}$ | $1.5 \times 10^3$ |
| 7 | 18.5 | 100 | $1.9 \times 10^{-9}$ | $4.6 \times 10^2$ |
| 8 | 18.5 | 300 | $5.6 \times 10^{-9}$ | $1.4 \times 10^3$ |
| 9 | 54.5 | 100 | $5.5 \times 10^{-9}$ | $1.4 \times 10^3$ |
| 10 | 54.5 | 900 | $4.9 \times 10^{-8}$ | $1.2 \times 10^4$ |

As can be seen from FIG. 2B, when the value of $D \times L_E/L_s^2$ is $3 \times 10^2$ or more, the carrier mobility variation is reduced. Specifically, when the value of $L_S/D$ is about 1, the source/drain electrodes 16 are bridged by one nanosheet [i.e., the sheet resistance value $R_{sheet}=R_{intra}$] and the source/drain electrodes 16 are bridged by a plurality of nanosheets [i.e., the sheet resistance value $R_{sheet}=(R_{intra}+R_{inter})$] at the same time, which causes the characteristic variation (see sample 1 and sample 2 of Table 1). Thus, by satisfying $D \times L_E \geqq 3 \times 10^2 \times L_s^2$ (i.e., by increasing the product of the interval D between the first electrode and the second electrode with the length $L_E$ of the first electrode and the second electrode (area occupied by the active layer 20) to a value $3\times10^2$ times or more larger than the average nanosheet area) (i.e., by allowing a great number of nanosheets to exist in the active layer 20), the sheet resistance value $R_{sheet}$ of the active layer 20 per unit length of the control electrode (the gate electrode 14) is averaged. Thus, it is possible to suppress a variation in electrical resistance value of the active layer 20 provided between the source/drain electrodes 16, thus suppressing a carrier mobility variation of the 3-terminal electronic device from occurring.

When $L_S/D \geq 10$ was established, the carrier mobility variation was 7% or less. Alternatively, when $D \times L_E \geq 3 \times 10^2 \times L_s^2$ was established, the carrier mobility variation was 7% or less. The suppression of the carrier mobility variation to a value equal to or lower than 7% empirically shows a reduced variation of the ON current. For example, when a 3-terminal electronic device (thin-film transistor) is used as a driving TFT for an organic electroluminescence display apparatus, a brightness variation between light-emitting elements can be easily compensated using a compensation circuit, with the result that a clear image having high uniformity can be displayed.

The following will describe the outline of the manufacture method for the 3-terminal electronic device (field effect transistor) of Example 1 with reference to FIGS. 1A and 1B that are schematic partial end views of the base body, for example.

A solution including the nanosheets 21 is prepared in advance. Specifically, graphite powders (100 mesh-passed product) of 500 milligrams were added to $NaNO_3$ of 382 milligrams, $H_2SO_4$ of 17 milliliters, and $KMO_4$ of 2.29 grams and these materials were agitated at room temperature for 5 days, thereby oxidizing graphite. Then, the resultant suspension liquid was diluted by 5 wt % of $H_2SO_4$ of 50 milliliters and 30 wt % of $H_2O_2$ was added in a few drips. Then, a supernatant subjected to centrifugal separation was substituted with a mixed solution of 3 wt % of $H_2SO_4$ and 0.5 wt % of $H_2O_2$ 10 times to thereby remove ions. By dispersing this precipitate in pure water, dispersion liquid of oxidized graphene (GO) was obtained. In order to completely remove acids and ions from the GO dispersion liquid, a dialysis was carried out for 60 hours. Then, the GO dispersion liquid was prepared to have pH of 10 and the concentration of 0.4 milligram/milliliter and then hydrazine (a weight ratio between GO and hydrazine of 1:1) was added thereto. The resultant liquid was reduced for one hour in argon gas atmosphere at 95° C. Thereafter, the dispersion liquid was immediately subjected to a dialysis to remove the remaining hydrazine to thereby obtain the RGO dispersion liquid (solution including the nanosheets 21).

[Step-100]

First, on the support body 10, the gate electrode 14 is formed. Specifically, on the insulating film 12 made of $SiO_2$ formed on the surface of the glass substrate 11, a resist layer (not shown) is formed by a lithography technique. In the resist layer, a part in which the gate electrode 14 is to be formed is removed. Thereafter, a titanium (Ti) layer (not shown) as a contact layer and a gold (Au) layer as the gate electrode 14 are sequentially formed on the entire surface by a vacuum vapor deposition method to subsequently remove the resist layer. In this manner, the gate electrode 14 can be obtained based on the so-called lift off method.

[Step-110]

Next, on the support body 10 including the gate electrode 14 (more specifically, the insulating film 12 formed on the surface of the glass substrate 11), the gate insulating film 15 corresponding to the base body 13 is formed. Specifically, the gate insulating film 15 made of SiO2 is formed on the gate electrode 14 and the insulating film 12 based on the sputtering method. During the formation of the gate insulating film 15, a part of the gate electrode 14 can be covered with a hard mask to thereby form an extraction section (not shown) of the gate electrode 14 without a photolithography process.

[Step-120]

Thereafter, on the gate insulating film 15, the source/drain electrodes 16 made of a gold (Au) layer are formed (see FIG. 1A). Specifically, the titanium (Ti) layer (not shown) as a contact layer having a thickness of about 0.5 nm and a gold (Au) layer as the source/drain electrodes 16 having a thickness of about 25 nm are sequentially formed based on the vacuum vapor deposition method. During the formation of these layers, a part of the gate insulating film 15 can be covered with a hard mask to thereby form the source/drain electrodes 16 without a photolithography process.

[Step-130]

Next, the active layer 20 is formed on the base body 13 using the above-described solution including the nanosheets 21 based on a coating method. Specifically, the solution including the nanosheets 21 prepared in advance is used to coat the solution including the nanosheets 21 on the entire surface by a spin coating method. Then, the solution including the nanosheets 21 is dried. As a result, the active layer 20 can be formed on the gate insulating film 15 and the source/drain electrodes 16 (see FIG. 1B).

[Step-140]

Finally, a passivation film (not shown) is formed on the entire surface to thereby obtain a bottom gate/bottom contact-type FET (specifically, TFT).

In the 3-terminal electronic device (specifically, FET) of Example 1 or Example 2 to Example 4 (which will be described later), a predetermined voltage is applied to the first electrode and the second electrode (the source/drain electrodes 16) and a voltage is additionally applied to the control electrode (the gate electrode 14), with the result that the current flowing in the active layer 20 can be controlled (or modulated).

Example 2

Example 2 is a modification of Example 1. In Example 2, the 3-terminal electronic device is a bottom gate/top contact-type FET (specifically, TFT). The field effect transistor of Example 2 includes, as shown in a schematic partial cross-sectional view of FIG. 4B:

(a) the gate electrode 14 formed on the support body 10 (which corresponds to the control electrode);

(b) the gate insulating film 15 formed on the gate electrode 14 and the support body 10 (which corresponds to the insulating layer and also corresponds to the base body 13);

(c) a channel formation region constituting layer 18 that is formed on the gate insulating film 15 and includes a channel formation region 17 composed by the active layer 20; and (d) the source/drain electrodes 16 formed on the channel formation region constituting layer 18 (which correspond to the first electrode and the second electrode).

The following will describe the outline of the manufacture method of the 3-terminal electronic device (field effect transistor) of Example 2 with reference to FIGS. 4A and 4B that are schematic partial end views of the base body, for example.

[Step-200]

First, as in [Step-100] of Example 1, the gate electrode 14 is formed on the support body 10. Then, as in [Step-110] of Example 1, the gate insulating film 15 corresponding to the base body 13 is formed on the support body including the gate electrode 14 (more specifically, the insulating film 12).

[Step-210]

Next, as in [Step-130] of Example 1, the active layer 20 is formed on the base body 13 (see FIG. 4A). In this manner, the channel formation region constituting layer 18 including the channel formation region 17 can be formed.

[Step-220]

Thereafter, the source/drain electrodes 16 are formed on the channel formation region constituting layer 18 so as to sandwich the channel formation region 17 (see FIG. 4B). Specifically, as in [Step-120] of Example 1, a titanium (Ti) layer (not shown) as a contact layer and a gold (Au) layer as the source/drain electrodes 16 are sequentially formed based on the vacuum vapor deposition method. During the formation of these layers, a part of the channel formation region constituting layer 18 can be covered with a hard mask to thereby form the source/drain electrodes 16 without a photolithography process.

[Step-230]

Finally, by forming a passivation film (not shown) on the entire surface, the 3-terminal electronic device of Example 2 can be completed.

Example 3

Example 3 is also a modification of Example 1. In Example 3, the 3-terminal electronic device is a top gate/bottom contact-type FET (specifically, TFT). The field effect transistor of Example 3 includes, as shown in a schematic partial cross-sectional view of FIG. 5B:

(a) the source/drain electrodes 16 formed on the insulating film 12 corresponding to the base body 13 (which correspond to the first electrode and the second electrode);

(b) the channel formation region 17 that is formed on the base body 13 between the source/drain electrodes 16 and is composed by the active layer 20;

(c) the gate insulating film 15 that is formed on the source/drain electrodes 16 and the channel formation region 17 (which corresponds to the insulating layer); and (d) the gate electrode 14 formed on the gate insulating film 15 (which corresponds to the control electrode).

The following will describe, with reference to schematic partial end views of the base body for example of FIGS. 5A and 5B, the outline of the manufacture method of the 3-terminal electronic device (field effect transistor) of Example 3.

[Step-300]

First, by the method as in [Step-120] of Example 1, the source/drain electrodes 16 are formed on the insulating film 12 corresponding to the base body 13. Thereafter, as in [Step-130] of Example 1, the active layer 20 is formed on the base body 13 including the source/drain electrodes 16 (more specifically, the insulating film 12) (see FIG. 5A).

[Step-310]

Next, the gate insulating film 15 is formed by the method as in [Step-110] of Example 1. Thereafter, the gate electrode 14 is formed on a part of the gate insulating film 15 on the channel formation region 17 by the method as in [Step-100] of Example 1 (see FIG. 5B).

[Step-320]

Finally, a passivation film (not shown) is formed on the entire surface, thereby completing the 3-terminal electronic device of Example 3.

Example 4

Example 4 is also a modification of Example 1. In Example 4, the 3-terminal electronic device is a top gate/top contact-type FET (specifically, TFT). The field effect transistor of Example 4 includes, as shown in a schematic partial cross-sectional view of FIG. 6C:

(a) the channel formation region constituting layer 18 that is formed on the insulating film 12 corresponding to the base body 13 and is composed by the active layer 20;

(b) the source/drain electrodes 16 formed on the channel formation region constituting layer 18 (which correspond to the first electrode and the second electrode);

(c) the gate insulating film 15 formed on the source/drain electrodes 16 and the channel formation region 17 (which corresponds to an insulating layer); and (d) the gate electrode 14 formed on the gate insulating film 15 (which corresponds to the control electrode).

The following will describe, with reference to schematic partial end views of the base body for example of FIGS. 6A to 6C, the outline of the manufacture method of the 3-terminal electronic device (field effect transistor) of Example 4.

[Step-400]

First, as in [Step-130] of Example 1, the active layer 20 is formed on the base body 13 (more specifically, the insulating film 12) (see FIG. 6A).

[Step-410]

Next, by the method as in [Step-120] of Example 1, the source/drain electrodes 16 are formed on the channel formation region constituting layer 18 (see FIG. 6B).

[Step-420]

Thereafter, the gate insulating film 15 is formed by the method as in [Step-110] of Example 1. Next, the gate electrode 14 is formed on a part of the gate insulating film 15 on the channel formation region 17 by the method as in [Step-100] of Example 1 (see FIG. 6C).

[Step-430]

Finally, a passivation film (not shown) is formed on the entire surface to thereby complete the 3-terminal electronic device of Example 4.

Example 5

Example 5 relates to the 2-terminal electronic device according to the first embodiment or the second embodiment (specifically, a chemical substance sensor for sensing $NO_2$ gas). The 2-terminal electronic device of Example 5 includes, as shown in the schematic partial cross-sectional view of FIG. 7A or 7B:

(A) a first electrode 116A and the second electrode 116B; and (B) an active layer 120 provided between the first electrode 116A and the second electrode 116B.

The active layer (chemical substance sensing layer) 120 is formed of a collection of the nanosheets 21. In the 2-terminal electronic device of Example 5 shown in FIG. 7A, the first electrode 116A and the second electrode 116B are formed on the base body 13. On the other hand, in the 2-terminal electronic device of Example 5 shown in FIG. 7B, a collection of the nanosheets 21 is present between the base body 13 and the first electrode 116A and second electrode 116B. When assuming that the nanosheets have the average size $L_S$ and the first electrode 116A and the second electrode 116B have the interval D therebetween, $L_S/D \geq 10$ is satisfied. Alternatively, when assuming that the nanosheets have the average size $L_S$, the first electrode 116A and the second electrode 116B have the interval D therebetween, and the first electrode 116A and the second electrode 116B each have the length $L_E$, $D \times L_E \geq 3 \times 10^2 \times L_S^2$ is satisfied. In the 2-terminal electronic device of Example 5, parts other than parts at which the active layer 120 is exposed are sealed by a resin layer (not shown).

Specifically, in the 2-terminal electronic device of Example 5, as in Example 1, the nanosheets 21 of $L_S$=2 μm were used to prepare a 2-terminal electronic device (chemical substance sensor) for which the interval D between the first electrode 116A and the second electrode 116B was set to 0.2 μm. The length $L_E$ of the first electrode 116A and the second electrode 116B was set to 100 μm.

Alternatively, in the 2-terminal electronic device of Example 5, the interval D between the first electrode 116A and the second electrode 116B was set to 2.5 μm and the length $L_E$ of the first electrode 116A and the second electrode 116B was set to 600 μm.

In the chemical substance sensor of Example 5, adsorption of to-be-sensed chemical substance by the active layer 120 causes a change in the electrical resistance value between the first electrode 116A and the second electrode 116B. Thus, current is caused to flow between the first electrode 116A and the second electrode 116B or an appropriate voltage is applied between the first electrode 116A and the second electrode 116B to measure the electrical resistance value of the active layer 120. Thus, the amount of the chemical substance (concentration) adsorbed by the active layer 120 can be measured. Since the chemical substance has an adsorption equilibrium status in the active layer 120, a temporal change in the amount of the chemical substance (concentration) in the atmosphere including the active layer causes a change in the equilibrium status.

In Example 5, $L_S/D \geq 10$ is also satisfied. Specifically, nanosheets that are sufficiently larger than the interval between the first electrode 116A and the second electrode 116B are arranged between the first electrode 116A and the second electrode 116B. Thus, as described in Example 1 based on the evaluation results of the relation between $L_S/D$ and the carrier mobility variation, it is possible to suppress a variation in the electrical resistance value of the active layer 120 provided between the first electrode 116A and the second electrode 116B, thus suppressing a characteristic variation of the 2-terminal electronic device from occurring. Alternatively, by establishing $D \times L_E \geq 3 \times 10^2 \times L_S^2$ (i.e., by allowing a great number of nanosheets to exist in the active layer 120), as described in Example 1 based on the evaluation results of the relation between $D \times L_E$ and the carrier mobility variation, it is possible to suppress a variation in the electrical resistance value of the active layer 120 provided between the first electrode 116A and the second electrode 116B, thus suppressing a characteristic variation of the 2-terminal electronic device from occurring.

Figure 7A:
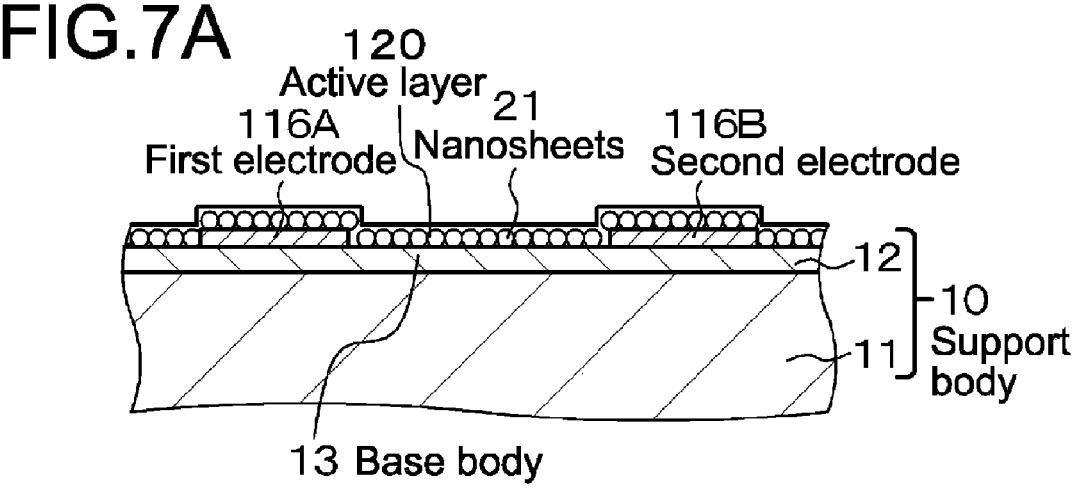
FIGS. 7A and 7B are schematic partial cross-sectional views illustrating a 2-terminal electronic device of Example 5.
Figure 7B:
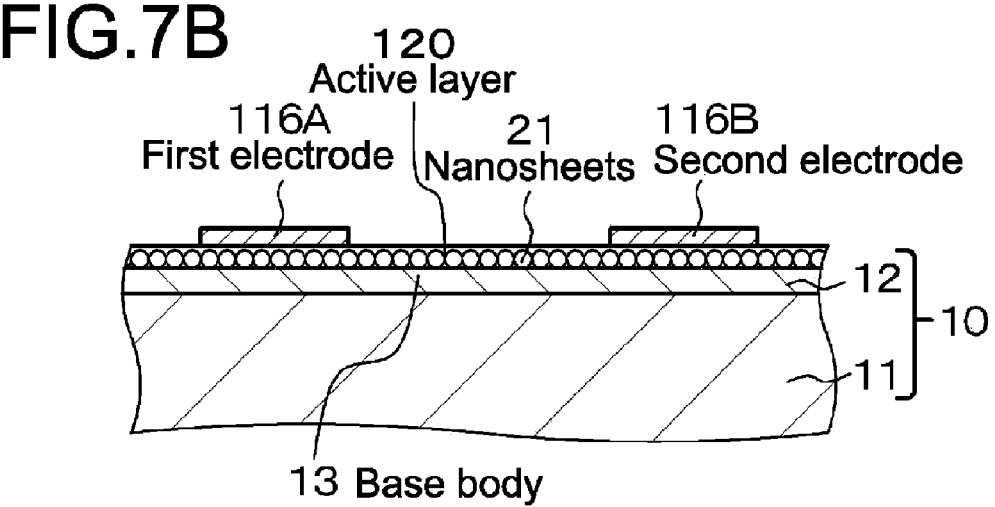

The 2-terminal electronic device of Example 5 shown in FIG. 7A can be substantially obtained by carrying out a step as in [Step-300] of Example 3. The 2-terminal electronic device of Example 5 shown in FIG. 7B can be substantially obtained by carrying out steps as in [Step-400] to [Step-410] of Example 4.

As described above, the present application has been described based on preferred embodiments. However, the present application is not limited to these embodiments. The structure and configuration of the electronic device, formation conditions, and manufacture conditions are illustrative and can be appropriately changed. In Examples, nanosheets of graphene (reduced graphene oxide) formed of one carbon atom layer were used. However, nanosheets formed of semiconductor material such as $MoS_2$, $SnS_2$, or GaSe can also be used. When a field effect transistor (FET) as a 3-terminal electronic device obtained by the present application is applied to and used for a display apparatus and various electronic devices for example, a monolithic integrated circuit in which a support body or a support member is integrated with a great number of FETs may be obtained or the respective FETs may also be cut and individuated and may be used as discrete parts.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

This application is claimed as follows:

1. A 3-terminal electronic device, comprising:
a control electrode;
a first electrode and a second electrode; and
an active layer that is provided between the first electrode and the second electrode and is provided to be opposed to the control electrode via an insulating layer,
wherein the active layer includes a collection of nanosheets, and
wherein when the nanosheets have an average size $L_S$ and the first electrode and the second electrode have an interval D therebetween, $L_S/D \geq 10$ is satisfied.

2. The 3-terminal electronic device according to claim 1, wherein the nanosheets are also formed on top of the first electrode and the second electrode.

3. The 3-terminal electronic device according to claim 1, wherein a carrier mobility variation is less than or equal to 7%.

4. A 2-terminal electronic device, comprising:
a first electrode and a second electrode; and
an active layer that is provided between the first electrode and the second electrode,
wherein the active layer includes a collection of nanosheets, and
wherein when the nanosheets have an average size $L_S$ and the first electrode and the second electrode have an interval D therebetween, $L_S/D \geq 10$ is satisfied.

5. The 2-terminal electronic device according to claim 4, wherein the nanosheets are also formed on top of the first electrode and the second electrode.

6. The 2-terminal electronic device according to claim 4, wherein a carrier mobility variation is less than or equal to 7%.

* * * * *